US008893722B2

(12) United States Patent
Emanuel (10) Patent No.: US 8,893,722 B2
(45) Date of Patent: Nov. 25, 2014

(54) SURGICAL ENDOSCOPIC CUTTING DEVICE AND METHOD FOR ITS USE

(75) Inventor: Mark Hans Emanuel, Bloemendaal (NL)

(73) Assignee: Smith & Nephew, Inc., Memphis, TN (US)

( * ) Notice: Subject to any disclaimer, the term of this patent is extended or adjusted under 35 U.S.C. 154(b) by 102 days.

(21) Appl. No.: 13/446,202

(22) Filed: Apr. 13, 2012

(65) Prior Publication Data

US 2012/0197280 A1    Aug. 2, 2012

Related U.S. Application Data

(60) Continuation of application No. 11/929,940, filed on Oct. 30, 2007, which is a division of application No. 11/780,759, filed on Jul. 20, 2007, now Pat. No. 8,061,359, which is a continuation of application No. 09/486,977, filed as application No. PCT/NL98/00504 on Sep. 4, 1998, now Pat. No. 7,249,602.

(30) Foreign Application Priority Data

Sep. 4, 1997    (NL) ..................................... 1006944

(51) Int. Cl.
*A61B 19/00*      (2006.01)
*A61B 17/32*      (2006.01)
(52) U.S. Cl.
USPC .............................. 128/898; 606/170; 606/15
(58) Field of Classification Search
USPC ........ 606/15, 170, 185, 22, 180; 604/22, 256; 128/898; 600/104, 127
See application file for complete search history.

(56) References Cited

U.S. PATENT DOCUMENTS

| | | |
|---|---|---|
| 1,831,786 A | 4/1926 | Duncan |
| 1,585,934 A | 5/1926 | Joseph |
| 1,666,332 A | 4/1928 | Hirsch |
| 2,708,437 A | 5/1955 | Hutchins |
| 3,297,022 A | 1/1967 | Wallace |
| 3,686,706 A | 8/1972 | Finley |
| 3,734,099 A | 5/1973 | Bender et al. |
| 3,791,379 A | 2/1974 | Storz |
| 3,812,855 A | 5/1974 | Banko et al. |
| 3,850,162 A | 11/1974 | Iglesias |

(Continued)

FOREIGN PATENT DOCUMENTS

| | | |
|---|---|---|
| DE | 3206381 | 9/1983 |
| DE | 3339322 | 5/1984 |

(Continued)

OTHER PUBLICATIONS

Amendment in Reply to Action of Jan. 5, 2010, dated Mar. 31, 2011 in the '359 patent file history ("Amendment and Response Dated Mar. 31, 2011").

(Continued)

*Primary Examiner* — Vy Q Bui
(74) *Attorney, Agent, or Firm* — Shayne Y. Huff; Ronald I. Eisenstein; Nixon Peabody LLP (57) ABSTRACT

A surgical endoscopic cutting device includes cutting elements fitted in a protective tube. The device has an inlet for fluid, a discharge outlet for tissue and fluid, and a further outlet that discharges most of the fluid.

4 Claims, 3 Drawing Sheets

(56) References Cited

U.S. PATENT DOCUMENTS

| | | |
|---|---|---|
| 3,945,375 A | 3/1976 | Banko |
| 3,980,252 A | 9/1976 | Tae |
| 3,995,619 A | 12/1976 | Glatzer |
| 3,996,921 A | 12/1976 | Neuwirth |
| 4,011,869 A | 3/1977 | Seiler, Jr. |
| 4,108,182 A | 8/1978 | Hartman et al. |
| 4,146,405 A | 3/1979 | Timmer et al. |
| 4,198,958 A | 4/1980 | Utsugi |
| 4,203,444 A | 5/1980 | Bonnell et al. |
| 4,210,146 A | 7/1980 | Banko |
| 4,246,902 A | 1/1981 | Martinez |
| 4,247,180 A | 1/1981 | Norris |
| 4,258,721 A | 3/1981 | Parent et al. |
| 4,261,346 A | 4/1981 | Wettermann |
| 4,294,234 A | 10/1981 | Matsuo |
| 4,316,465 A | 2/1982 | Dotson |
| 4,369,768 A | 1/1983 | Vukovic |
| 4,392,485 A | 7/1983 | Hiltebrandt |
| 4,414,962 A | 11/1983 | Carson |
| 4,449,538 A | 5/1984 | Corbitt et al. |
| 4,493,698 A | 1/1985 | Wang et al. |
| 4,517,977 A | 5/1985 | Frost |
| 4,543,965 A | 10/1985 | Pack et al. |
| 4,567,880 A | 2/1986 | Goodman |
| 4,589,414 A | 5/1986 | Yoshida et al. |
| 4,601,290 A | 7/1986 | Effron et al. |
| 4,606,330 A | 8/1986 | Bonnet |
| 4,630,598 A | 12/1986 | Bonnet |
| 4,644,952 A | 2/1987 | Patipa et al. |
| 4,649,919 A | 3/1987 | Thimsen et al. |
| 4,700,694 A | 10/1987 | Shishido |
| 4,706,656 A | 11/1987 | Kuboto |
| 4,718,291 A | 1/1988 | Wood et al. |
| 4,737,142 A | 4/1988 | Heckele |
| 4,749,376 A | 6/1988 | Kensey et al. |
| 4,756,309 A | 7/1988 | Sachse et al. |
| 4,819,635 A | 4/1989 | Shapiro |
| 4,844,064 A | 7/1989 | Thimsen et al. |
| 4,850,354 A | 7/1989 | McGurk-Burleson et al. |
| 4,856,919 A | 8/1989 | Takeuchi et al. |
| 4,867,157 A | 9/1989 | McGurk et al. |
| 4,924,851 A | 5/1990 | Ognier et al. |
| 4,940,061 A | 7/1990 | Terwilliger et al. |
| 4,950,278 A | 8/1990 | Sachse et al. |
| 4,955,882 A | 9/1990 | Hakky |
| 4,986,827 A | 1/1991 | Akkas et al. |
| 4,998,527 A | 3/1991 | Meyer |
| 4,998,914 A | 3/1991 | Wiest et al. |
| 5,007,917 A | 4/1991 | Evans |
| 5,027,792 A | 7/1991 | Meyer |
| 5,037,386 A | 8/1991 | Marcus et al. |
| 5,105,800 A | 4/1992 | Takahashi et al. |
| 5,106,364 A | 4/1992 | Hayafuji et al. |
| 5,112,299 A | 5/1992 | Pascaloff |
| 5,116,868 A | 5/1992 | Chen et al. |
| 5,125,910 A | 6/1992 | Freitas |
| 5,133,713 A | 7/1992 | Huang et al. |
| 5,152,744 A | 10/1992 | Krause et al. |
| 5,158,553 A | 10/1992 | Berry et al. |
| 5,163,433 A | 11/1992 | Kagawa et al. |
| 5,169,397 A | 12/1992 | Sakashita et al. |
| 5,176,677 A | 1/1993 | Wuchinich |
| 5,195,541 A | 3/1993 | Obenchain |
| 5,226,910 A | 7/1993 | Kajiyama et al. |
| 5,244,459 A | 9/1993 | Hill |
| 5,254,117 A | 10/1993 | Rigby et al. |
| 5,269,785 A | 12/1993 | Bonutti |
| 5,270,622 A | 12/1993 | Krause |
| 5,275,609 A | 1/1994 | Pingleton et al. |
| 5,288,290 A | 2/1994 | Brody |
| 5,304,118 A | 4/1994 | Trese et al. |
| 5,312,399 A * | 5/1994 | Hakky et al. .................. 606/15 |
| 5,312,425 A | 5/1994 | Evans et al. |
| 5,312,430 A | 5/1994 | Rosenbluth et al. |
| 5,320,091 A | 6/1994 | Grossi et al. |
| 5,347,992 A | 9/1994 | Pearlman et al. |
| 5,350,390 A | 9/1994 | Sher |
| 5,364,395 A | 11/1994 | West |
| 5,374,253 A | 12/1994 | Burns et al. |
| 5,390,585 A | 2/1995 | Ryuh |
| 5,392,765 A | 2/1995 | Muller |
| 5,395,313 A | 3/1995 | Naves et al. |
| 5,403,276 A | 4/1995 | Schechter et al. |
| 5,409,013 A | 4/1995 | Clement |
| 5,411,513 A | 5/1995 | Ireland et al. |
| 5,425,376 A | 6/1995 | Banys et al. |
| 5,429,601 A | 7/1995 | Conley et al. |
| 5,443,476 A | 8/1995 | Shapiro |
| 5,449,356 A | 9/1995 | Walbrink et al. |
| 5,456,689 A | 10/1995 | Kresch et al. |
| 5,490,819 A | 2/1996 | Nicholas et al. |
| 5,490,860 A | 2/1996 | Middle et al. |
| 5,492,537 A | 2/1996 | Vancaillie |
| 5,498,258 A | 3/1996 | Hakky et al. |
| 5,527,331 A | 6/1996 | Kresch et al. |
| 5,549,541 A | 8/1996 | Muller |
| 5,556,378 A | 9/1996 | Storz et al. |
| 5,563,481 A | 10/1996 | Krause |
| 5,569,164 A | 10/1996 | Lurz |
| 5,569,254 A | 10/1996 | Carlson et al. |
| 5,569,284 A | 10/1996 | Young et al. |
| 5,591,187 A | 1/1997 | Dekel |
| 5,601,583 A | 2/1997 | Donahue et al. |
| 5,602,449 A | 2/1997 | Krause et al. |
| 5,603,332 A | 2/1997 | O Connor |
| 5,630,798 A | 5/1997 | Beiser et al. |
| 5,649,547 A | 7/1997 | Ritchart et al. |
| 5,669,927 A | 9/1997 | Boebel et al. |
| 5,672,945 A | 9/1997 | Krause |
| 5,674,179 A | 10/1997 | Bonnet et al. |
| 5,676,497 A | 10/1997 | Kim |
| 5,695,448 A | 12/1997 | Kimura et al. |
| 5,702,420 A | 12/1997 | Sterling et al. |
| 5,709,698 A | 1/1998 | Adams et al. |
| 5,730,752 A | 3/1998 | Alden et al. |
| 5,733,298 A | 3/1998 | Berman et al. |
| 5,741,286 A | 4/1998 | Recuset |
| 5,741,287 A | 4/1998 | Alden et al. |
| 5,749,885 A | 5/1998 | Sjostrom et al. |
| 5,749,889 A | 5/1998 | Bracich et al. |
| 5,759,185 A | 6/1998 | Grinberg |
| 5,772,634 A | 6/1998 | Atkinson |
| 5,775,333 A | 7/1998 | Burbank et al. |
| 5,782,849 A | 7/1998 | Miller |
| 5,807,240 A | 9/1998 | Muller et al. |
| 5,807,282 A | 9/1998 | Fowler |
| 5,810,861 A | 9/1998 | Gaber |
| 5,814,009 A | 9/1998 | Wheatman |
| 5,833,643 A | 11/1998 | Ross et al. |
| 5,840,060 A | 11/1998 | Beiser et al. |
| 5,857,995 A | 1/1999 | Thomas et al. |
| 5,873,886 A | 2/1999 | Larsen et al. |
| 5,899,915 A | 5/1999 | Saadat |
| 5,911,699 A | 6/1999 | Anis et al. |
| 5,911,722 A | 6/1999 | Adler et al. |
| 5,913,867 A | 6/1999 | Dion |
| 5,916,229 A | 6/1999 | Evans |
| 5,925,055 A | 7/1999 | Adrian et al. |
| 5,928,163 A | 7/1999 | Roberts et al. |
| 5,944,668 A | 8/1999 | Vancaillie et al. |
| 5,947,990 A | 9/1999 | Smith |
| 5,951,490 A | 9/1999 | Fowler |
| 5,956,130 A | 9/1999 | Vancaillie et al. |
| 5,957,832 A | 9/1999 | Taylor et al. |
| 6,001,116 A | 12/1999 | Heisler et al. |
| 6,004,320 A | 12/1999 | Casscells et al. |
| 6,007,513 A | 12/1999 | Anis et al. |
| 6,024,751 A * | 2/2000 | Lovato et al. .................. 606/170 |
| 6,032,673 A | 3/2000 | Savage et al. |
| 6,039,748 A | 3/2000 | Savage et al. |
| 6,042,552 A | 3/2000 | Cornier |
| 6,068,641 A | 5/2000 | Varsseveld |
| 6,086,542 A | 7/2000 | Glowa et al. |
| 6,090,123 A | 7/2000 | Culp et al. |

(56) References Cited

U.S. PATENT DOCUMENTS

| | | |
|---|---|---|
| 6,113,594 A | 9/2000 | Savage |
| 6,119,973 A | 9/2000 | Galloway |
| 6,120,147 A | 9/2000 | Vijfvinkel et al. |
| 6,120,462 A | 9/2000 | Hibner et al. |
| 6,132,448 A | 10/2000 | Perez et al. |
| 6,149,633 A | 11/2000 | Maaskamp |
| 6,156,049 A | 12/2000 | Lovato et al. |
| 6,159,160 A | 12/2000 | Hsei et al. |
| 6,159,209 A | 12/2000 | Hakky |
| 6,203,518 B1 | 3/2001 | Anis et al. |
| 6,217,543 B1 | 4/2001 | Anis et al. |
| 6,224,603 B1 | 5/2001 | Marino |
| 6,244,228 B1 | 6/2001 | Kuhn et al. |
| 6,258,111 B1 | 7/2001 | Ross et al. |
| 6,277,096 B1 | 8/2001 | Cortella et al. |
| 6,358,200 B1 | 3/2002 | Grossi |
| 6,358,263 B2 | 3/2002 | Mark et al. |
| 6,359,200 B1 | 3/2002 | Day |
| 6,402,701 B1 | 6/2002 | Kaplan et al. |
| 6,428,486 B2 | 8/2002 | Ritchart et al. |
| 6,494,892 B1 | 12/2002 | Ireland et al. |
| 6,585,708 B1 | 7/2003 | Maaskamp |
| 6,610,066 B2 | 8/2003 | Dinger et al. |
| 6,626,827 B1 | 9/2003 | Felix et al. |
| 6,632,182 B1 | 10/2003 | Treat |
| 6,656,132 B1 | 12/2003 | Ouchi |
| 6,712,773 B1 | 3/2004 | Viola et al. |
| 6,837,847 B2 | 1/2005 | Ewers et al. |
| 7,025,732 B2 | 4/2006 | Thompson et al. |
| 7,150,713 B2 | 12/2006 | Shener et al. |
| 7,226,459 B2 | 6/2007 | Cesarini et al. |
| 7,249,602 B1 | 7/2007 | Emanuel |
| 7,510,563 B2 | 3/2009 | Cesarini et al. |
| 7,763,033 B2 | 7/2010 | Gruber et al. |
| 7,922,737 B1 | 4/2011 | Cesarini et al. |
| 8,061,359 B2 | 11/2011 | Emanuel |
| 2001/0039963 A1 | 11/2001 | Spear et al. |
| 2001/0047183 A1 | 11/2001 | Privitera et al. |
| 2002/0058859 A1 | 5/2002 | Brommersma |
| 2003/0050603 A1 | 3/2003 | Todd |
| 2003/0050638 A1 | 3/2003 | Yachia et al. |
| 2003/0078609 A1 | 4/2003 | Finlay et al. |
| 2003/0114875 A1 | 6/2003 | Sjostrom |
| 2005/0043690 A1 | 2/2005 | Todd |
| 2005/0085692 A1 | 4/2005 | Kiehn et al. |
| 2006/0036132 A1 | 2/2006 | Renner |
| 2006/0047185 A1 | 3/2006 | Shener et al. |
| 2006/0241586 A1 | 10/2006 | Wilk |
| 2008/0015621 A1 | 1/2008 | Emanuel |
| 2008/0058588 A1 | 3/2008 | Emanuel |
| 2008/0058842 A1 | 3/2008 | Emanuel |
| 2008/0097468 A1 | 4/2008 | Adams et al. |
| 2008/0097469 A1 | 4/2008 | Gruber et al. |
| 2008/0097470 A1 | 4/2008 | Gruber et al. |
| 2008/0097471 A1 | 4/2008 | Adams et al. |
| 2008/0135053 A1 | 6/2008 | Gruber et al. |
| 2008/0146872 A1 | 6/2008 | Gruber et al. |
| 2008/0146873 A1 | 6/2008 | Adams et al. |
| 2008/0245371 A1 | 10/2008 | Gruber |
| 2008/0249366 A1 | 10/2008 | Gruber et al. |
| 2008/0249534 A1 | 10/2008 | Gruber et al. |
| 2008/0249553 A1 | 10/2008 | Gruber et al. |
| 2008/0262308 A1 | 10/2008 | Prestezog et al. |
| 2009/0270812 A1 | 10/2009 | Litscher et al. |
| 2009/0270895 A1 | 10/2009 | Churchill et al. |
| 2009/0270896 A1 | 10/2009 | Sullivan et al. |
| 2009/0270897 A1 | 10/2009 | Adams et al. |
| 2009/0270898 A1 | 10/2009 | Chin et al. |
| 2010/0087798 A1 | 4/2010 | Adams et al. |
| 2010/0152647 A1 | 6/2010 | Shener et al. |

FOREIGN PATENT DOCUMENTS

| | | |
|---|---|---|
| DE | 3601453 | 9/1986 |
| DE | 3615694 | 11/1987 |
| DE | 4038398 | 6/1992 |
| DE | 4440035 | 5/1996 |
| DE | 19633124 | 5/1997 |
| DE | 102006022827 | 12/2006 |
| EP | 0310285 | 9/1988 |
| EP | 0327410 | 8/1989 |
| EP | 0557044 | 8/1993 |
| EP | 0582295 | 8/1993 |
| EP | 0606531 | 9/1993 |
| EP | 0621008 | 4/1994 |
| EP | 0806183 | 5/1997 |
| GB | 2093353 | 9/1982 |
| GB | 2311468 | 10/1997 |
| JP | 1-75416 | 5/1989 |
| JP | 01-75416 | 5/1989 |
| JP | 2002529185 | 9/2002 |
| JP | 2003245247 | 9/2003 |
| NL | 1006944 | 5/1999 |
| WO | 81/01648 | 6/1981 |
| WO | 92/11816 | 7/1992 |
| WO | 93/07821 | 4/1993 |
| WO | 93/15664 | 8/1993 |
| WO | 94/26181 | 11/1994 |
| WO | 95/05777 | 3/1995 |
| WO | 95/10981 | 4/1995 |
| WO | 95/10982 | 4/1995 |
| WO | 95/30377 | 11/1995 |
| WO | 96/11638 | 4/1996 |
| WO | 96/26676 | 9/1996 |
| WO | 97/09922 | 3/1997 |
| WO | 97/17027 | 5/1997 |
| WO | 97/19642 | 6/1997 |
| WO | 97/24071 | 7/1997 |
| WO | 97/34534 | 9/1997 |
| WO | 97/35522 | 10/1997 |
| WO | 98/09569 | 3/1998 |
| WO | 98/10707 | 3/1998 |
| WO | 98/46147 | 10/1998 |
| WO | 99/03407 | 1/1999 |
| WO | 99/03409 | 1/1999 |
| WO | 99/07295 | 2/1999 |
| WO | 9911184 | 3/1999 |
| WO | 99/39648 | 8/1999 |
| WO | 99/44506 | 9/1999 |
| WO | 99/60935 | 12/1999 |
| WO | 00/12010 | 3/2000 |
| WO | 00/28890 | 5/2000 |
| WO | 00/33743 | 6/2000 |
| WO | 00/44295 | 8/2000 |
| WO | 00/47116 | 8/2000 |
| WO | 00/57797 | 10/2000 |
| WO | 01/35831 | 5/2001 |
| WO | 01/58368 | 8/2001 |
| WO | 01/95810 | 12/2001 |
| WO | 02/069808 | 9/2002 |
| WO | 03/022164 | 3/2003 |
| WO | 03/077767 | 9/2003 |
| WO | 2005/060842 | 7/2005 |
| WO | 2005/096963 | 10/2005 |
| WO | 2006/121968 | 11/2006 |
| WO | 2006/121970 | 11/2006 |
| WO | 2007/044833 | 4/2007 |

OTHER PUBLICATIONS

Amendment in Reply to Action of Jul. 26, 2010, dated Oct. 25, 2010 in the '359 patent file history ("Oct. 25, 2010 Response").

Baggish et al., "Instrumentation for Hysteroscopy," in "Diagnostic and Operative Hysterectomy," Mosby (1999).

Baggish et al., "Accessory Instruments for Operative Hysteroscopy," in "Diagnostic and Operative Hysterectomy," Mosby (1999).

Baggish et al., "Hysteroscopic Sterilization," in "Daignostic and Operative Hysterectomy," Mosby (1999).

Claim chart for anticipation of claims 1-8 based on Kresch '689.

Claim chart for anticipation of claims 1-8 based on Savage '673.

(56) References Cited

OTHER PUBLICATIONS

Claim chart for anticipation of claims 1-8 based on Banko '375.
Cravello et al., Hysteroscopic Resection fo Fibroids: Results with a 6-Year Follow-up Period, 15:1, Journal of Gynecologic Surgery, 1-5 (1999).
Defendant Hologic Inc.'s Preliminary, Non-Binding List of Asserted Prior Art References in *Smith & Nephew, Inc.* v. *Hologic, Inc.* Civil Action Nos. 11-CV-12064-RWZ and 10-CV-10951-RWZ, U.S. District Court for the District of Massachusetts, Feb. 8, 2012, 8 pages.
Dictionary definition of reciprocate, Merrian-Webster Dictionary, on-line edition, retrieved Mar. 20, 2013.
Dictionary definition of rotate, Merriam-Webster Dictionary, on-line edition, retrieved Mar. 20, 2013.
Dictionary definition of translate, Merriam-Webster Dictionary, on-line edition, retreived Mar. 20, 2013.
Drews et al., Surgical Approach to Myomas: Laparoscopy and Hysteroscopy, 10:4, Seminars in Reproductive Endocrinology, 367-77 (1992).
Dumesic et al., A New Approach to Hysteroscopic Cannulation of the Fallopian Tube, 7 Journal of Gynecologic Surgery, 7-9 (1991).
Emanuel et al., Long-term Results of Hysteroscopic Myomectomy for Abnormal Uterine Bleeding, 93:5 Obstet Gynecoogy, 743-748 (1999).
Executed Expert Declaration of Hal Walbrink in support of Request for Inter Partes Reexamination of U.S. Patent No. 8,061,359.
Executed Expert Declaration of Dr. Henry A. Dominicis in support of Request for Inter Partes Reexamination of U.S. Patent No. 8,061,359.
Exhibit P to Hologic's Opposition to Smith & Nephew's Motion for Preliminary Injunction, Redacted, *Smith & Nephew, Inc.* v. *Hologic, Inc.* Civil Action No. 11-CV-12064-RWZ, filed Dec. 30, 2011.
Franchini et al., Endometrial Resection: A Diagnostic Tool in Postmenopausal Women, 8 Gynecological Endoscopy, 111-14 (1999).
Gerber S, et al., The Endoscapel: A New Endoscopic Instrument for Supracervical Hysterectomy and Morcellation of Masses: Clinical Evaluation, 86: Suppl. 1, European Journal of Obstetrics & Gynecology and Reproductive Biology, S9-S31 (1999).
Gregory Bacsko, Uterine Surgery by Operative Hysteroscopy, 71 European Journal of Obstetrics Gynecology and Reproductive Biology, 219-222 (1997).
GYNECARE X-TRACT, "Tissue Morcellator", Instruction for Use.
GYNECARE "Motor Drive Unit" Instructions for Use.
Gynescope: Laser Fiber Director, Advertisement, Journal of Gynecologic Surgery, vol. 6 (1990).
Hologic's Opposition to Smith & Nephew's Motion for Preliminary Injunction, Redacted, *Smith & Nephew, Inc.* v. *Hologic, Inc.*, Civil Action No. 11-CV-12064-RWZ, filed Dec. 30, 2011.
International search report and written opinion regarding International patent application PCT/US2011/053753 mailed on Dec. 20, 2011.
Japanese Office Action in Application No. 2007-530014, dated Feb. 15, 2011.
Karl Storz, Advertisement, Journal of Gynecologic Surgery, vol. 5 (1989).
Karl Storz Uterine Resectoscopes for Endometrial Ablation and Resection, Advertisement, Journal of Gynecologic Surgery, vol. 6 (1990).
Lin et al., Clinical Applications of a New Fujinon Operating Fiberoptic Hysteroscope, 6 Journal of Gynecologic Surgery, 81-87 (1990).
Mettler et al., Pelviscopic Uterine Surgery 6 Surgical Endoscopy, 23-31 (1992).
Neis et al., "Hysteroscopy: Texytbook and Atlas" 91-103, Thieme Medical Publishers (1994).
Nisolle et al., Endometrial Ablation with the Nd-VAG Laser in Dysfunctional Bleeding 1 Minimally Invasive therapy, 35-39 (1991).
Office Action dated Sep. 7, 2005 in the '602 patent file history ("Sep. 7, 2005 Office Action").
Office Action dated Jul. 22, 2010 in the '359 patent file history ("Jul. 22, 2010 Office Action").
Office Action dated Jan. 5, 2011 in the '359 patent file history ("Final Action dated Jan. 5, 2011").
Office Action in U.S. Appl. No. 11/929,940 mailed Jul. 1, 2010.
Office Action in U.S. Appl. No. 11/929,940 mailed Dec. 30, 2009.
Office Action in U.S. Appl. No. 11/780,759, mailed Jul. 26, 2010.
Office Action for U.S. Appl. No. 11/780,759 mailed Jan. 5, 2011.
Office Action for U.S. Appl. No. 11/929,938, mailed Jan. 5, 2011.
Office Action for U.S. Appl. No. 11/929,938, mailed Jul. 30, 2010.
Opening Claim Construction Brief of Defendant HOLOGIC, Inc., from Massachusetts Civil Action No. 1:11-cv-12064-RWZ (Defendant's Opening Markman Brief.).
Opening Markman Brief of Plaintiff Smith & Nephew, Inc., from Massachusetts Civil Action No. 1:11-cv-12064-RWZ "Plaintiff's Opening Markman Brief").
Park et al., Endoscopic Management of Uterine Myoma 40: 6 Yonsei Medical Journal, 583-88 (1999).
Reference AQ "Fishing Reel produced and sold by Shimano of Japan in to the U.S. prior to Oct. 26, 2001," as cited in the IDS filed Oct. 17, 2005 in the prosecution file history of U.S. Appl. No. 09/983,810, 7 pages.
Request for Inter Partes Reexamination of U.S. Patent No. 8,061,359, filed Apr. 2, 2012.
Reexamination Litigation Search Report (CRU 3999) filed Apr. 2, 2012.
Sheath et al., Fiberoptic Light for Oophorectomy at Vaginal Hysterectomy 14 Journal of Gynecologic Surgery, 119-22 (1998).
Sugimoto et al., "A Color Atlas of Hysteroscopy" 6-7 Springer, (1999).
U.S. Advisory Action in U.S. Appl. No. 11/929,940, mailed Sep. 10, 2010.
Valle et al., Hysteroscopic Removal of Submucous Leiomyomas 6:2 Journal fo Gynecologic Surgery, 89-96 (1990).
Weck, A Squibb Company: Direct Path to Diagnostic and Operative Control, Advertisement, Journal of Gynecologic Surgery, vol. 7 (1991).
Williamson et al., Editorial 1: Complications of Hysteroscopic treatments of Menorrhagia, 77:3 British Journal of Anesthesia, 305-308 (1996).
Wolf, "Morce-Power 2306 Electronic Morcellator" (2 pages).
Decision Granting Request for Reexam mailed Jun. 5, 2012.
Office Action for U.S. Appl. No. 95/002,933 mailed Jun. 5, 2012.
Patent Owner's Response to Office Action for U.S. Appl. No. 95/002,933 mailed Jun. 5, 2012.
Third Party Requester's Response to Office Action for U.S. Appl. No. 95/002,933 mailed Jun. 5, 2012.
Office Action for U.S. Appl. No. 95/001,933 mailed Apr. 1, 2013.
Patent Owner's Response to Office Action for U.S. Appl. No. 95/001,933 mailed Apr. 1, 2013.
Third Party Requester's Response to Office Action for U.S. Appl. No. 95/001,933 mailed Apr. 1, 2013.
Office Action for U.S. Appl. No. 95/001,933 mailed Sep. 19, 2013.
Patent Owner's Response to Office Action for U.S. Appl. No. 95/001,933 mailed Sep. 19, 2013.
International search report for International Application No. PCT/US2005/029807 Jun. 13, 2006.
"From Distention to Deficit Monitoring Taking the All-In-One Approach," W.O.M. World of Medicine.
Karl Storz, "Pilot a Course to Successful outcome," 2001 Intermetro Industries Corporation.
GYNECARE, "Fluid Management System" Instruction for Use.
C.R. Bard, Inc, "The HydroFlex HD System".
"HysteRo-Purator 1143-1 Technical Data."
Richard Wolf "The Fluid Manager".
ACMI Corporation, "Dolphin II and DESTIN-U-FLO Fluid Management Systems for Hysteroscopy", ACMI Corporation 2002.
ACMI Corporation, "Dolphin II Hysteroscopic Fluid Management Systems," ACMI Corporation 2002.
European Patent Office Examination Report for Application No. 05 786 521.4-2305 dated Apr. 21, 2010, 4 pages.
European Patent Office Examination Report for Application No. 05 786 521.4-2305 dated Sep. 26, 2010, 5 pages.
PCT International Preliminary Report on Patentability for Application No. PCT/US2005/029807 dated Feb. 28, 2007, 9 pges.

(56) References Cited

OTHER PUBLICATIONS

Notice of Reasons for Rejection of Japanese Application No. 207-530014, mailed Feb. 7, 2012, 2 pages.

Textbook of Biliopancreatic Disease (W. Hess and G. Berci, eds., PICCIN 1997), e.g., Fig. 6.5.1, 1584-1586.

3rd Party Response to ACP sent Sep. 19, 2013 for U.S. Appl. No. 95/001,933.

Right of Appeal Notice sent Jan. 14, 2014 for U.S. Appl. No. 95/001,933.

Denial of Petition for U.S. Appl. No. 95/001,955 mailed Sep. 28, 2012.

Denial of Order for U.S. Appl. No. 95/001,955 mailed Jun. 4, 2012.

Petition for Review for U.S. Appl. No. 95/001,955, Jul. 3, 2012.

Third Party Response to Action Closing Prosecution for U.S. Appl. No. 95/002,058.

Third Party Response to First Office Action for U.S. Appl. No. 95/002,058.

Action Closing Prosecution for U.S. Appl. No. 95/002,058 sent Aug. 9, 2013.

First Office Action for U.S. Appl. No. 95/002,058 mailed Sep. 19, 2012.

Patent Owner's Response to First Office Action for U.S. Appl. No. 95/002,058 mailed Sep. 19, 2012.

Patent Owner's Response to Action Closing Prosecution for U.S. Appl. No. 95/002,058.

Reexam Order for U.S. Appl. No. 95/002,058 mailed Sep. 19, 2012.

Second Office Action for U.S. Appl. No. 95/002,058 mailed Jan. 24, 2014.

\* cited by examiner

SURGICAL ENDOSCOPIC CUTTING DEVICE AND METHOD FOR ITS USE

CROSS-REFERENCE TO RELATED APPLICATIONS

This application is a continuation of U.S. patent application Ser. No. 11/929,940, filed Oct. 30, 2007, abandoned, which is a divisional application of U.S. application Ser. No. 11/780,759, filed on Jul. 20, 2007, now U.S. Pat. No. 8,061,359, which is a continuation application of U.S. application Ser. No. 09/486,977, filed on Mar. 6, 2000, now U.S. Pat. No. 7,249,602, which is a national phase of PCT/NL98/00504, filed Sep. 4, 1998, which claims priority from Netherlands Application No. 1006944, filed Sep. 4, 1997. The contents of the prior applications are incorporated herein by reference in their entirety.

FIELD OF THE INVENTION

The present invention relates to a surgical endoscopic cutting device.

BACKGROUND OF THE INVENTION

Surgical cutting devices are generally known and used for the removal of hard and/or soft tissue, such as in the vicinity of the knee joint. Such cutting devices are used in, for example, a joint cavity, where they can be guided endoscopically by separately inserting a viewing device having a light source and an observation portion. Such operations are successfully used in organs and joints lying not too deep underneath the skin.

When operations are being carried out on organs lying deeper, other techniques are currently used. If, for example, tissue has to be removed from the uterus, prostate, or urinary bladder, such as mucous membrane or other tissues, it was customary until now to use a so-called "loop." This is a loop-shaped cutting wire which is brought to a first potential, while the wall of the uterus is brought to a second, different potential. Tissue is removed by moving the loop along the uterus wall. In order to be able to carry out such an operation, it is necessary to dilate the uterus. Dilation is carried out by introducing a fluid. In order to maintain the effect of the potential difference, a non-conducting fluid is used, for example a 5% sorbitol solution. Because wounds are caused during the treatment described above, a good part of this fluid is resorbed into the patient's bloodstream (by way of the uterus). This can lead to highly dangerous electrolyte displacements. It has been found that the tissue can be removed more easily by working with a high-frequency monopolar electric current, but there is a risk of high-frequency electric current leading to internal and external burns. The loop is generally fitted on an endoscope and moved back and forth along the uterus wall with the endoscope. The tissue cut off during this treatment has to be removed from the uterus, which considerably extends the duration of the operation. Furthermore, the doctor has to check that all detached material actually has been removed.

This means that such operations are very time-consuming and require the surgeon to repeatedly move the device back and forth. This is tiring and consequently difficult to learn. Moreover, the patient has to be monitored continually during the operation, in order to prevent the undesirable phenomena described above. It is not uncommon for such an operation to be broken off because the patient's life is endangered by the side effects.

On the other hand, it is desirable to be able to carry out such operations instead of simply performing a hysterectomy.

WO 96/11638 discloses a cutter including a hollow stem and a cutting head accommodated inside a rigid housing. This rigid housing likewise contains a viewing channel with the necessary optics. U.S. Pat. No. 5,195,541 describes a laparoscopic discectomy apparatus. For a laparoscopic method it is essential to inflate the related cavity using gas. The gas feed is discontinuous and has no effect on viewing of the operation site.

Fluid is introduced by way of a space between the stem and the rigid housing and discharged together with the detached tissue through the hollow stem of the cutter.

This device could be satisfactory for the removal of tissues from certain body cavities, such as from the bladder. However, in the case of other body cavities, it is necessary to "blow up" the cavity before treatment can be carried out. An example of this is the uterus, in which it is important that the amount of enlargement of the organ be accurately controlled. The irregular discharge of fluid through the hollow stem of the cutter, caused partly by the irregular release of tissue, means that it cannot be guaranteed that the pressure inside the cavity is accurately controlled.

Such a device is consequently not very suitable for use in the treatment of such a cavity.

SUMMARY OF THE INVENTION

The object of the present invention is to provide a device which can perform such a treatment.

According to the invention, a further outlet channel is provided, the function of which is independent of whether or not detached tissue has been released. In other words, a regular discharge of fluid can occur through this further outlet channel. Since only a minor part of the fluid is now discharged through the outlet, in which there are detached pieces of tissue, the pressure inside the body cavity can be regulated and controlled accurately. This makes it possible to remove undesired tissue from cavities such as the uterus. The applicability of the removal of tissues by cutting is consequently considerably increased.

The further outlet channel described above is formed by an insertion tube fitted around the endoscopic device. This insertion tube serves to clear a space for the endoscopic device. For this purpose, the front side of the insertion tube can be provided with an insertion mandrel, which is removed after the positioning of the insertion tube and replaced by the endoscopic device described above. In this case the further outlet channel can be defined between the endoscopic device and the insertion tube.

In the case of such a construction it is desirable for a coupler to be present to provide a coupling between the rigid housing and the insertion tube described above.

Discharge of the tissue material which has been detached can be achieved either by making the stem on which the cutting elements are fitted hollow, or by fitting a protective tube around the cutter. Such a protective tube can also be used without the space between protective tube and stem serving as an outlet channel. This means that the cutter can be designed as a separate unit which can be coupled to the rigid housing, which has advantages in particular for purposes of sterilization. Namely, the device can then be detached in a simple way.

For the removal of tissue from a uterus it is essential for the rigid housing to have a length which is sufficient to reach all tissue parts, i.e. a length of at least 30 cm.

The observation part of the device described above includes a light channel in the housing, provided near one end with a lens and near the other end with an observation mechanism. The latter can include an eyepiece or a connection for a camera so that the surgeon can carry out the operation using a monitor and others can possibly look at the same time.

The cutting elements described above can include any cutting element known in the prior art. In other words, a cutting head with cutting faces can be used, but it is also possible to use constructions with teeth, meshing with the protective tube or otherwise. In the latter instance, the protective tube is preferably provided with a lateral opening through which a part of the cutting elements extends so that on each revolution, part of the tissue is removed and can be discharged directly through the interior of the drive/discharge tube of the cutter.

The invention also relates to a method for the removal of uterus tissue in which the device described above is used. In other words, a machining operation is now applied with the use of a physiological fluid which can be electrically conducting without any problem, while at the same time the removed tissue is sucked out. It is, of course, possible to suck out the tissue at a later stage. The machining operation is carried out by a rotating action.

According to a further embodiment of the method, an outlet and a further outlet are present, and the pressure inside the body cavity is regulated by metering the quantity of fluid which moves through the further outlet. The insertion of the surgical endoscopic cutting device is preferably carried out in the manner described above using an insertion mandrel and insertion tube.

BRIEF DESCRIPTION OF DRAWINGS

The invention will be explained in greater detail below with reference to an exemplary embodiment shown in the drawings, in which:

FIG. 3 shows a partially cut-away perspective view of the device of FIG. 1, with the insertion end enlarged;

DETAILED DESCRIPTION

Figures 1, 1A:
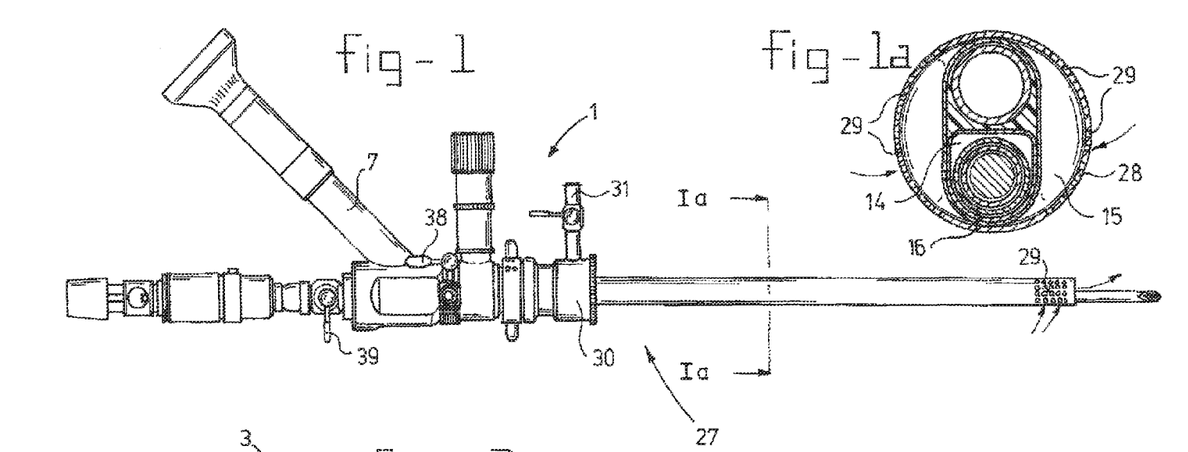
FIG. 1 shows the endoscopic cutting device according to the invention in the assembled state, in side view and partially in section.
FIG. 1a shows the viewing/receiving part of the cutting device of FIG. 1 in section along the line Ia-Ia.

The endoscopic cutting device according to the invention is indicated in its entirety by 1 in FIG. 1. It comprises a viewing/receiving part 3, which is shown in FIG. 2, a cutting part 2, which is shown in greater detail in FIGS. 4 and 5, and an insertion mandrel, which is shown in FIG. 6.

Figure 2:
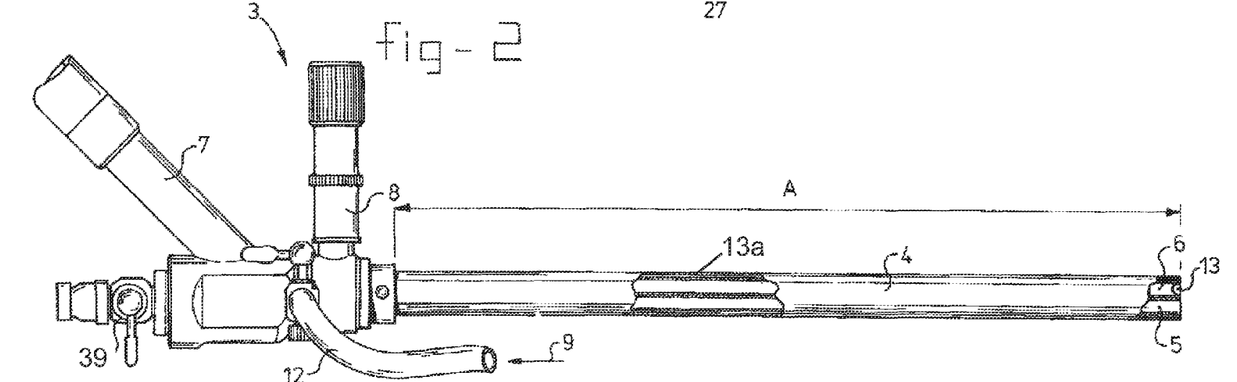
FIG. 2 shows a side and partially cut-away view of the viewing/receiving part of the cutting device of FIG. 1.

With reference to FIG. 2, it can be seen that the viewing/receiving part 3, is composed of an outer tube 4 in which a main channel 5 and viewing channel 6 are defined. Viewing channel 6 ends at one side in a lens 13 and at the other side in a viewing tube 7, on which an eyepiece or camera connection is placed. A connection 8 for a light source is also present, for connection to a fibre optics bundle which provides for lighting at the end of lens 13. Near the control end, tube 4 is provided with a fluid inlet 9 connected to a hose 12, for adding a physiological salt solution.

A shut-off valve is indicated by 10.

The length of the actual outer tube 4, is indicated by A and is more than 30 cm.

Figure 4:
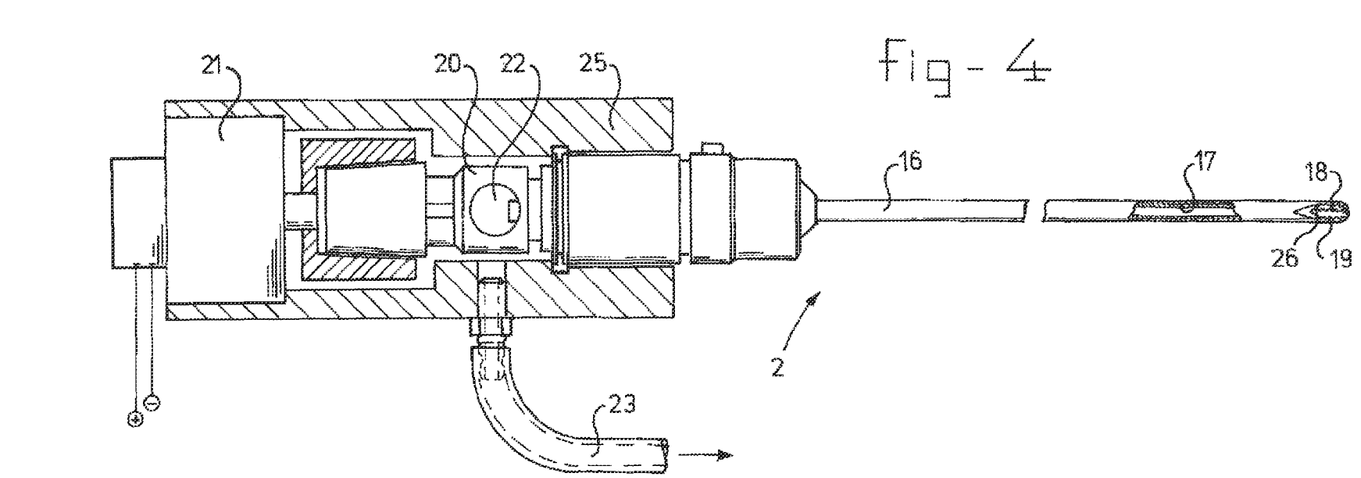
FIG. 4 shows a partially sectional side view of the cutter of the cutting device of FIG. 3.

FIG. 4 shows details of the cutter or the cutting part 2, which is composed of a protective tube 16 inside of which a drive/suction tube 17 is fitted. Near the working end, tube 17 is provided with teeth 19 which mesh with teeth 18 provided in an opening 26 in the end part of protective tube 16. Near the other end, drive/suction tube 17 is provided with a coupling 20, which can be connected at one end to a rotating drive motor 21, not shown in detail, and at the other end is provided with an opening 22 through which fluid and removed material can be discharged by way of suction tube 17 to the discharge hose 23. A pressure regulator can be present in this discharge hose 23, which is connected to a vacuum source.

In FIG. 1 the insertion part is indicated by 27. This insertion part is composed of an insertion tube 28 which is provided with openings 29 at one end and near the other end, the insertion part 27 is provided with a bayonet connection 30 and an outlet 31. Insertion tube 28 is designed in such a way that tube 4 can be fitted therein, as shown in FIGS. 1 and 3, while it is also possible to fit insertion mandrel 40, provided with stem 41 and mandrel 42, in insertion tube 28

The construction described above has an inlet 38 for fluid. Inlet 38 extends to channel 14 (FIG. 1a), i.e. the space bounded between the outer tube 4 and the protective tube 16 and 36, respectively from FIG. 4 or 5. A shut-off valve 39, which is connected to channel 14, is present, while the further outlet is indicated by 31. A discharge hose 23 for tissue and fluid is shown. During the removal of tissue, with a substantially continuous supply of fluid through inlet 38, some of the fluid will be discharged through outlet 23. This relatively small amount will be mixed with a mixture released during the cutting operation. Most of the fluid will be discharged through the further outlet 31. This discharge is unimpeded and occurs through openings 29. Pressure variations occurring due to the presence or absence of removed tissue in channel 17 (FIG. 4) have little or no influence on the pressure inside the body cavity owing to the presence of the further outlet 31.

If the device is to be inserted into, for example, a uterus, insertion mandrel 40 will first be inserted, with shut-off valve 39 open, into insertion tube 28 with bayonet 30. This assembly is then placed in the uterus in a relatively simple manner due to the shape of mandrel 42. Mandrel 42 is then removed by manipulating stem 41, and the construction shown in FIG. 2 is placed in tube 28. Connection is made here to bayonet 30. The cutting action can then begin after the uterus has been dilated by the introduction of fluid. This fluid can be a physiological flushing and distension fluid, such as a physiological salt solution (NaCl 0.9%). In the event of the (unavoidable) resorption of the physiological fluid into the blood, electrolyte displacement, with fatal consequences for the patient, will not occur. Owing to the absence of electrical current, the burns described above are also ruled out.

By switching on motor 21, tube 17 is set in rotation and teeth 19 move regularly along cutting edge 18 of protective tube 16 which remains stationary. While they are moving along each other and picking up tissue material between them, a cutting, detaching action on the tissue material is occurring. The cut, detached material is removed through the interior of tube 17 and outlet 23.

The appropriate area of the uterus can be treated by moving parts 18 and 19 along the uterus wall or along tissue to be removed, which can be observed through viewing tube 7 by supplying light through connection 8.

Through the use of a continuous flow system, a constantly clear view is obtained for the observer even if blood and/or mucous is/are in the mixture. Moreover, the pressure can be maintained as low as possible, in order to prevent intravasation.

Figure 5:
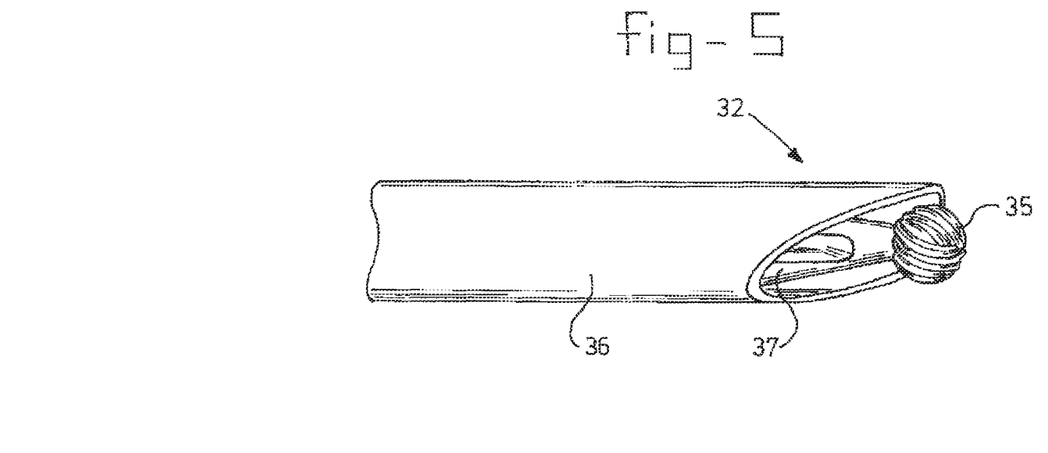
FIG. 5 shows a variant of the cutter shown in FIG. 4.
Figures 6, 7:
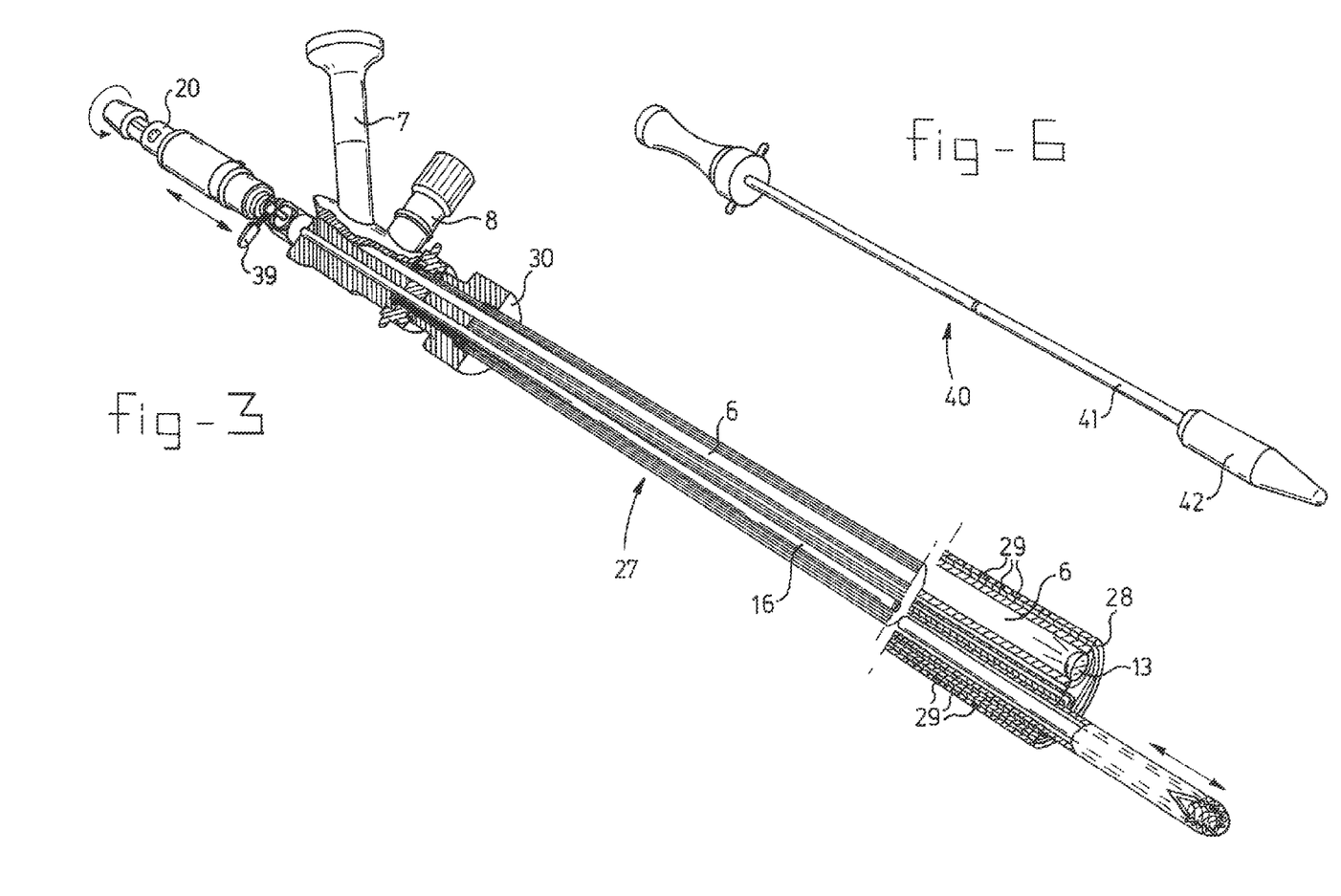
FIG. 6 shows an insertion mandrel according to the invention.

FIG. 5 shows a variant of the end of the cutter. The cutter or cutting part are indicated in their entirety by 32. The protective tube is indicated by 36 and is beveled near the end. The drive/suction tube is indicated by 37 and provided with a cutting head near the end. In this embodiment, there is either no interaction between cutting head 35 and protective tube 36, or head 35 and tube 36 interact near the edge of tube 36, which is adapted for that purpose by grinding.

It is understood that such cutting elements can be designed in any way known in the prior art.

These and further modifications are considered to lie within the scope of the present application, to be immediately obvious to the person skilled in the art after reading the description, and to lie within the scope of the appended claims. For instance, it is possible to effect the supply of working fluid and the discharge of cleaning material in another way, i.e., to arrange the interior of housing 4 slightly differently. Furthermore, the method described above can be used for the removal of other tissue material, such as prostate tissue through the urethra, or for the removal of tissue from the wall of the urinary bladder.

What is claimed is:

1. A method for the removal of tissue from a prostate gland, comprising:
    inserting an insertion tube including a first valve into the prostate gland;
    inserting an endoscope into the insertion tube to form an assembly, the endoscope including a second valve and an elongated member defining discrete first and second channels extending from a proximal region of the elongated member to a distal region of the elongated member, the first channel having a light guide permanently affixed therein, the second channel having a proximal end in communication with the second valve such that fluid from the second valve is able to flow into and through the second channel to a distal surgical site through an opening of the second channel at a distal face of a distal tip of the assembly, and the endoscope, when received within the insertion tube, forming a third channel bounded by an outer wall of the endoscope and an inner wall of the insertion tube such that fluid from the surgical site is able to flow into and through the third channel to the first valve through an opening of the third channel at the distal face of the distal tip of the assembly;
    inserting into the prostate gland and through the second channel of the endoscope a motor driven cutter for cutting and detaching tissue;
    introducing a fluid into the prostate gland through the second valve and the second channel; and
    aspirating fluid with detached tissue from the prostate gland through the inner tube of the cutter.

2. The method of claim 1, wherein the motor driven cutter includes an outer tube defining a window having teeth at a distal region of the outer tube and an inner tube received within the outer tube, the inner tube including a cutting element at a distal region of the inner tube configured to cut tissue at the window.

3. A method for the removal of tissue from a prostate gland, comprising:
    inserting into the prostate gland an insertion tube including a first valve for discharging fluid from the prostate gland;
    inserting an endoscope into the insertion tube, the endoscope including a port, a second valve, and an elongated member defining discrete first and second channels extending from a proximal region of the elongated member to a distal region of the elongated member, the first channel having a light guide permanently affixed therein, the port being in communication with the second channel to enable insertion of a motor driven cutter into the second channel through the port, and the second valve being in communication with the second channel to enable fluid flow into the prostate gland through the second valve and the second channel;
    inserting into the prostate gland and through the port and the second channel the motor driven cutter for cutting and detaching tissue;
    introducing fluid into the prostate gland through the second valve and the second channel; and
    aspirating fluid with detached tissue from the prostate gland through the inner tube of the cutter.

4. The method of claim 3, wherein the motor driven cutter includes an outer tube defining a first window at a distal region of the outer tube and an inner tube received within the outer tube, the inner tube defining a second window at a distal region of the inner tube, the second window having teeth and being configured to move relative to the first window to cut tissue at the first cutting window.

* * * * *